United States Patent [19]

Saitoh et al.

[11] Patent Number: 5,783,997
[45] Date of Patent: Jul. 21, 1998

[54] CARDIAC RATE MEASURING APPARATUS

[75] Inventors: Satoshi Saitoh; Mitsuo Yasushi, both of Kawagoe, Japan

[73] Assignee: Pioneer Electronic Corporation, Tokyo, Japan

[21] Appl. No.: 557,860

[22] Filed: Nov. 14, 1995

[30] Foreign Application Priority Data

Nov. 16, 1994 [JP] Japan ........................ 6-282220

[51] Int. Cl.⁶ .................................................. G08B 23/00
[52] U.S. Cl. ........................ 340/576; 128/689; 128/734; 340/425.5
[58] Field of Search ...................... 340/576, 438, 340/439, 425.5; 364/424.045; 280/748; 297/464, 216.1; 73/432.1, 862, 626; 307/10.1; 128/696, 689, 774, 734, 782

[56] References Cited

U.S. PATENT DOCUMENTS

| | | | |
|---|---|---|---|
| 4,664,127 | 5/1987 | Ikeyama | 128/689 |
| 4,706,072 | 11/1987 | Ikeyama | 340/576 |
| 4,928,090 | 5/1990 | Yoshimi et al. | 128/734 |
| 5,078,134 | 1/1992 | Heilman et al. | 128/734 |
| 5,404,128 | 4/1995 | Ogino et al. | 340/425.5 |

*Primary Examiner*—Jeffery A. Hofsass
*Assistant Examiner*—John Tweel, Jr.
*Attorney, Agent, or Firm*—Perman & Green, LLP

[57] ABSTRACT

A cardiac rate measuring apparatus which is intended to measure the cardiac rate of a driver without restraining motions of the driver. Skin tremors occurring on the surface of skin of the body are detected, and level peak values of the skin tremors are held to generate an envelope waveform signal as a cardiac rate signal corresponding to the cardiac rate of the driver.

1 Claim, 18 Drawing Sheets

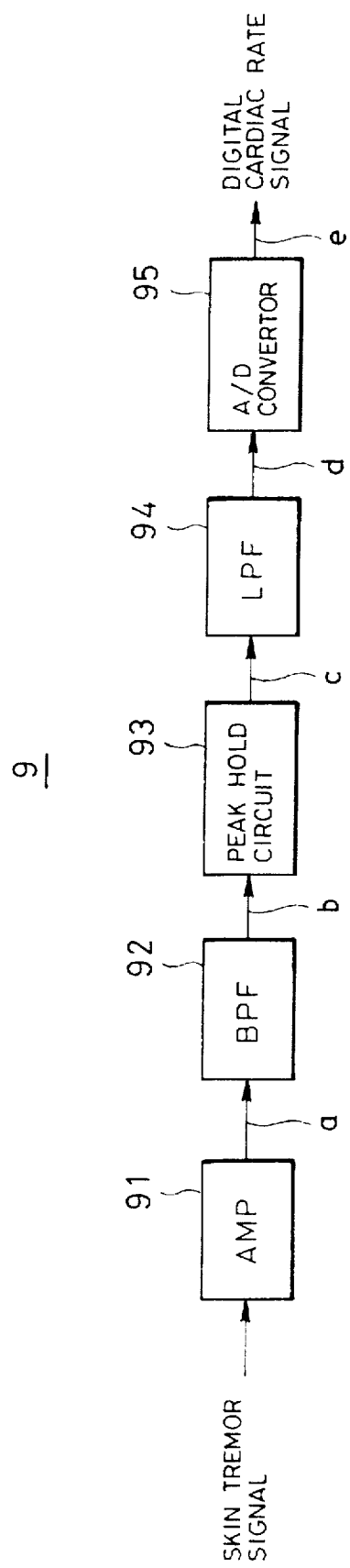

FIG.11

| | |
|---|---|
| C1 | RR1 |
| C2 | RR2 |
| C3 | RR3 |
| C4 | RR4 |
| ---- | ---- |

| | |
|---|---|
| B1 | $S \cdot n1$ |
| B2 | $(1/\sigma_a + 1/\sigma_u) \cdot n2$ |
| B3 | 0 OR n3 |
| B4 | $(RSA/MWSA) \cdot n4$ |
| B5 | $D \cdot n5$ |
| B6 | $Pn$ |
| B7 | $S \cdot h1$ |
| B8 | $(HRs - HR) \cdot h2$ |
| B9 | $(MWSA/RSA) \cdot h3$ |
| BA | $Ph$ |
| BB | $(S/L) \cdot e1$ |
| BC | $(MWSA/RSA) \cdot e2$ |
| BD | $Pe$ |

| | |
|---|---|
| A1 | STARTING TIME Ts |
| A2 | INITIAL NUMBER OF HEARTBEATS HRs |
| A3 | CURRENT NUMBER OF HEARTBEATS HR |
| A4 | MWSA |
| A5 | RSA |
| A6 | CURRENT TIME T |
| A7 | CONTINUOUS DRIVING TIME S |
| A8 | ORIENTATION VARIANCE $1/\sigma_a$ |
| A9 | SPEED VARIANCE $1/\sigma_u$ |
| AA | TRAVELLING DISTANCE L |
| AB | CURRENT RUNNING ROAD INFORMATION D |
| AC | SLEEPINESS OCCURRING TIME T1 |
| AD | SLEEPINESS OCCURRING TIME T2 |

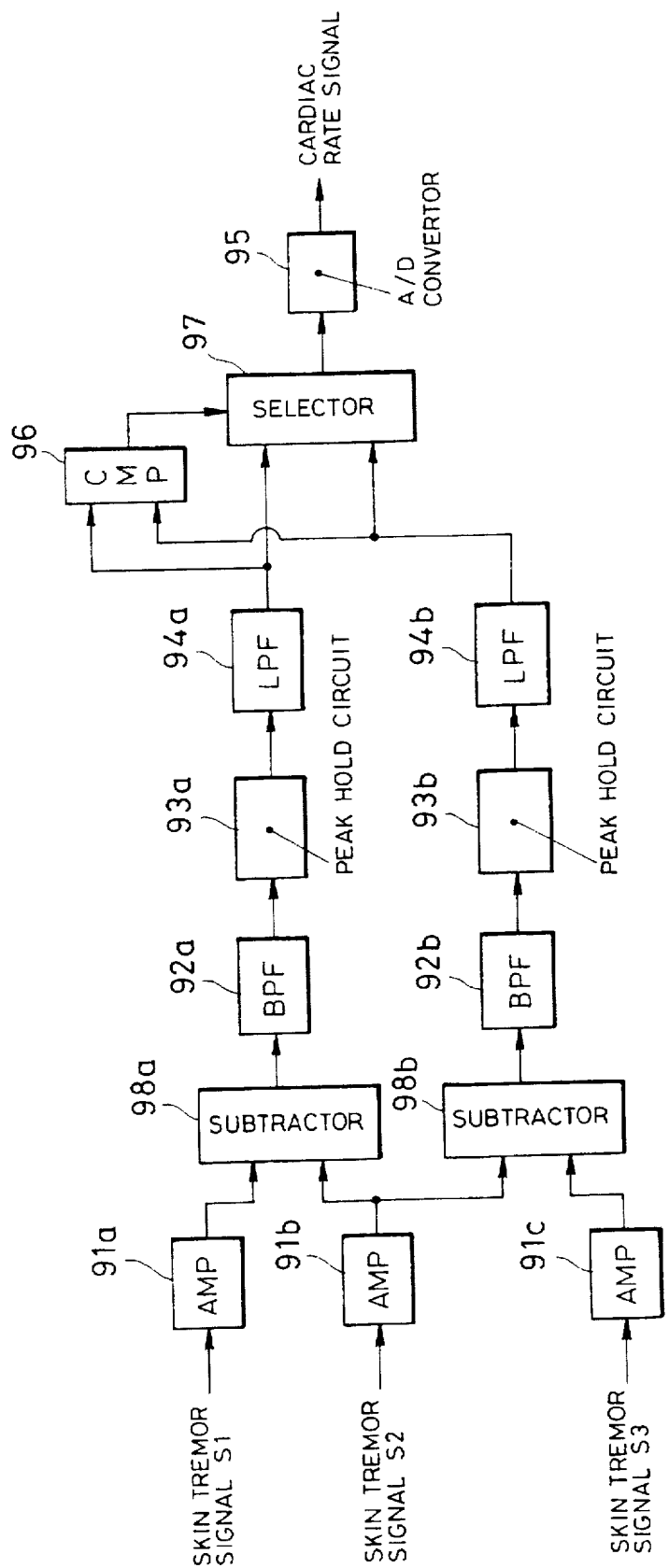

CARDIAC RATE MEASURING APPARATUS

BACKGROUND OF THE INVENTION

1. Field of the Invention

The present invention relates to a cardiac rate measuring apparatus, and more particularly to a cardiac rate measuring apparatus for measuring driver's cardiac rate during the drive of a vehicle.

2. Description of Background Information

In recent years, developments have been in progress for a driving condition detecting apparatus which detects sleepiness, tiredness, impatience and so on of a driver of a vehicle during the drive, and informs the driver of such conditions to promote safety driving.

In this event, the driving condition detecting apparatus measures the cardiac rate of a driver during the drive of a vehicle and determines his mental conditions such as sleepiness, tiredness, impatience, and so on based on the cardiac rate.

However, in order to measure the driver's cardiac rate, electrodes for detecting the cardiac rate must be directly attached on the breast or on the tips of fingers of the driver. Such electrodes cause a problem that motions of the driver are prevented by the electrodes under the car driving situation.

OBJECT AND SUMMARY OF THE INVENTION

The present invention has been made to solve the problem mentioned above, and its object is to provide a cardiac rate measuring apparatus which is capable of measuring a cardiac rate of a driver during the drive of a vehicle without restricting motions of the driver.

The cardiac rate measuring apparatus according to the present invention comprises skin tremor detecting means for detecting tremors of the skin of a body to generate a skin tremor signal, and a cardiac rate detecting means for holding level peak values of the skin tremor signal to generate an envelope waveform signal as a cardiac rate signal.

Skin tremors occurring on the surface of the skin of a body are detected, and peak level values of the skin tremor signal are held to generate an envelope waveform signal as a cardiac rate signal.

BRIEF DESCRIPTION OF THE DRAWINGS

FIG. 4 is a diagram showing the internal configuration of a cardiac rate detector circuit 9 in the cardiac rate measuring apparatus of the present invention;

FIG. 11 is a diagram showing a memory map for a RAM 13;

FIGS. 18–20 are diagrams showing other embodiments of the cardiac rate detector circuit 9 in the cardiac rate detecting apparatus of the present invention.

DESCRIPTION OF THE PREFERRED EMBODIMENTS

Figure 1:
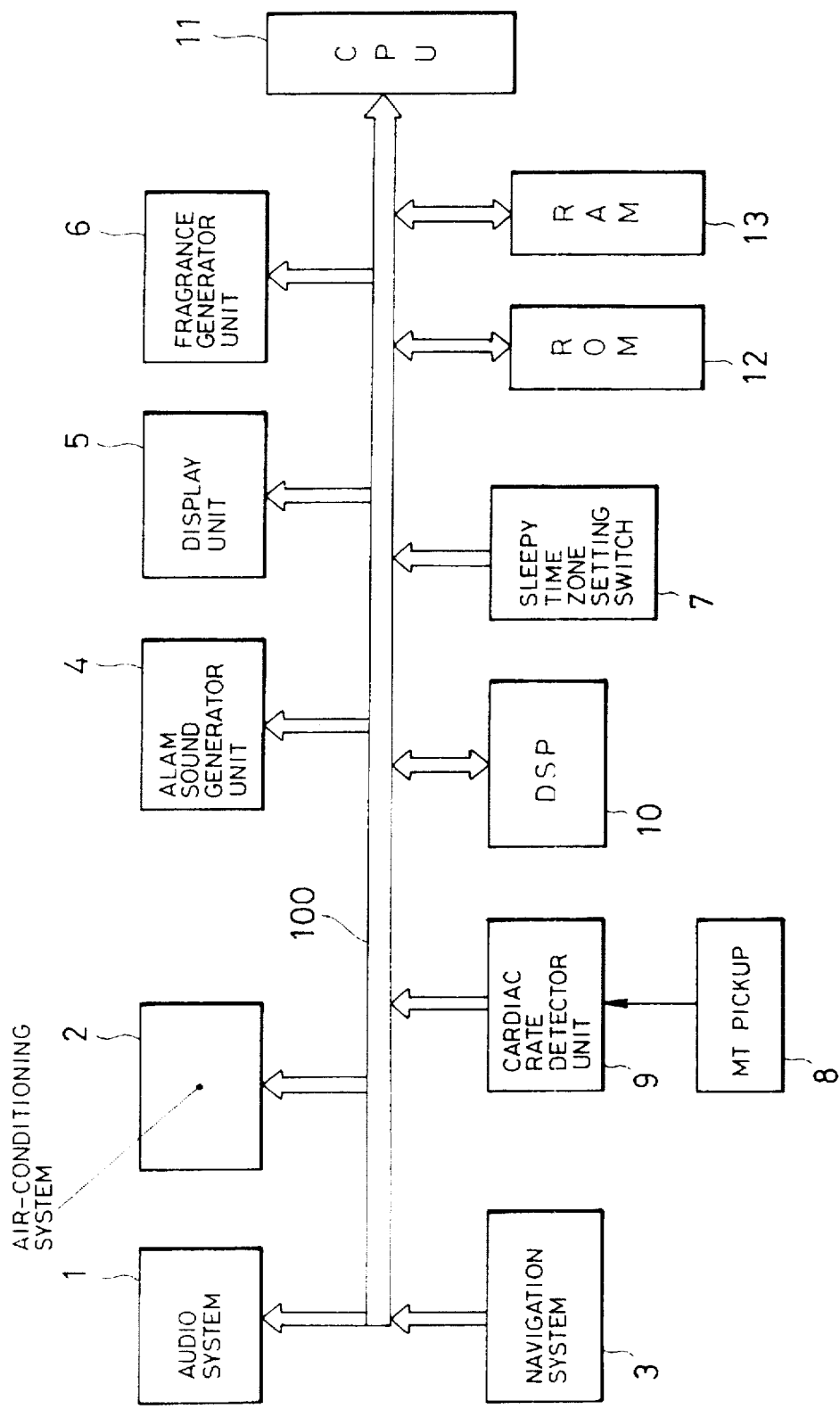
FIG. 1 is a diagram showing the configuration of a car accessory system in which a cardiac rate measuring apparatus of the present invention is implemented.

FIG. 1 shows the configuration of a car accessory system in which a cardiac rate measuring apparatus according to the present invention is implemented. Referring specifically to FIG. 1, an audio system 1 is a so-called car audio system which comprises components such as a CD player, a tuner, a cassette deck, an equalizer, an amplifier, speakers, and so on. The operations of these respective components of the car audio system 1 may be controlled by various operator manipulations and by various command signals supplied to these components through a CPU bus 100. An air conditioning system 2 is a so-called car air-conditioner for adjusting the temperature and humidity within a car. The air-conditioning system 2 has a temperature sensor for detecting the temperature within the car, and automatically adjusts the temperature within the car at a predetermined set temperature based on the temperature detected by the temperature sensor. More particularly, to adjust the temperature within the car, either warm air or cooling air may be blown into the car until the detected temperature becomes equal to the predetermined set temperature. In this event, the air-conditioning system 2 not only performs the automatic temperature adjusting operation as described above but also is controlled its operations in response to a variety of operation instructing signals supplied thereto through the CPU bus 100. The air-conditioning system 2 sends the detected temperature information obtained by the temperature sensor to the CPU bus 100.

Figure 2:
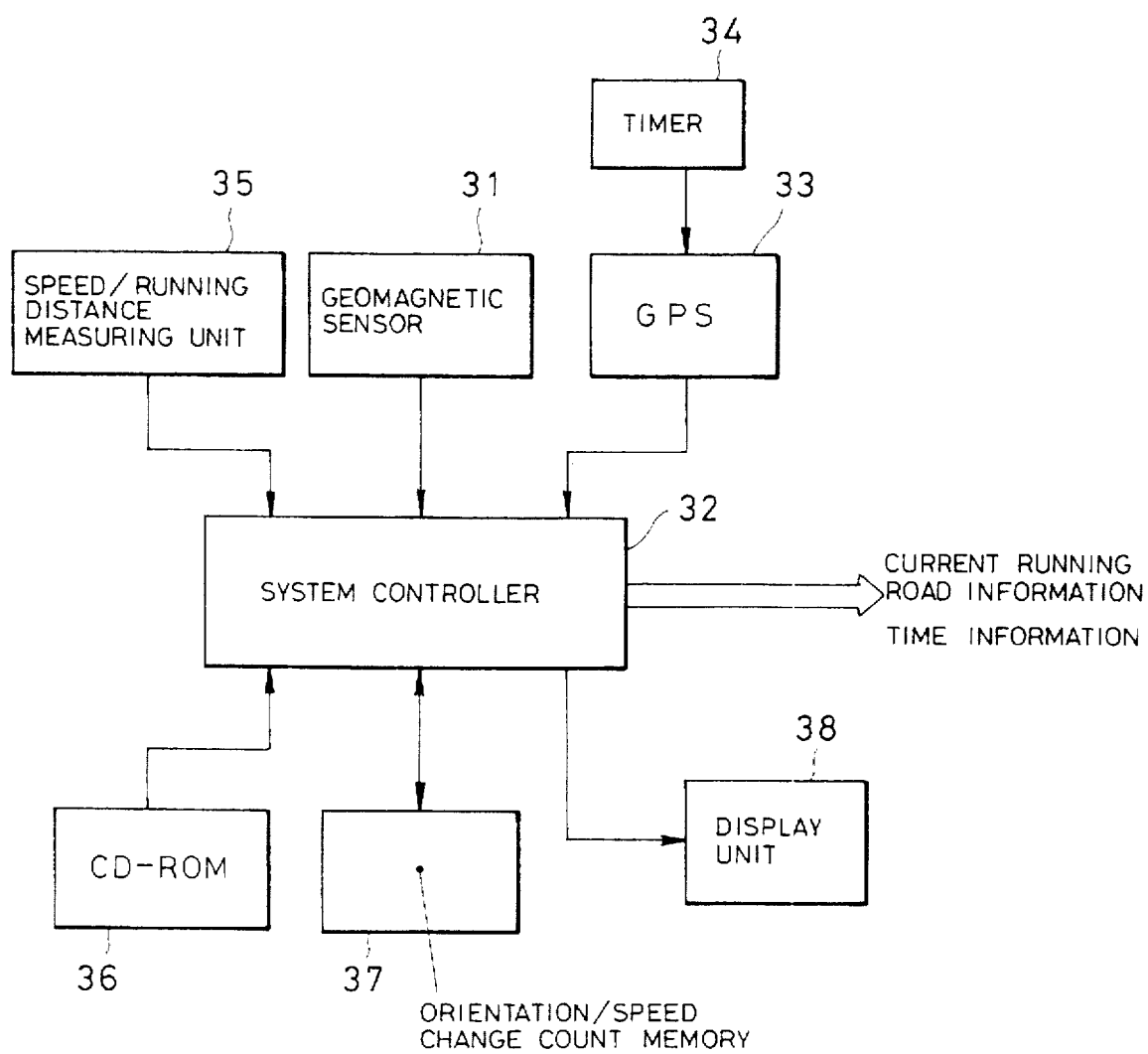
FIG. 2 is a diagram showing an exemplary configuration of a navigation system 3.

A navigation system 3 is an ordinary car navigation system which detects a current location of a car and links the detected current location to map information to display the current location on a display, thereby guiding the car to a predetermined destination. FIG. 2 is a diagram showing an exemplary configuration of the navigation system 3 as mentioned above.

Referring specifically to FIG. 2, a geomagnetic sensor 31 detects a geomagnetic (earth magnetic field) condition at the current location of the car, generates orientation information corresponding to a running direction of the car based on the detected geomagnetic condition, and supplies the orientation information to a system controller 32. A Global Positioning System (GPS) unit 33 receives current time information supplied from a timer 34 and distance measuring signals transmitted from a plurality of GPS satellites, measures the longitude and latitude of the current location of the car, and supplies the system controller 32 with longitude and latitude information. A speed/running distance measuring unit 35 measures the running speed of the car and an accumulated running distance from the time the engine of the car has been started, and supplies the system controller 32 with running speed information and accumulated running distance information. It should be noted that signals transmitted from GPS satellites also include time data in addition to a distance measuring signal as positional information, so that the timer 34 is not necessary if the current time is known from this time data. Also, if the accumulated running distance from the start of the car engine is calculated from the starting position and the current position of the car, and if the car speed is calculated from the distance of a certain interval and an elapsed time as an average speed in the interval, the speed/running distance measuring unit 35 is not necessary.

A CD-ROM player 36 reads information from a recording disc which has a map information and a variety of road information recorded thereon, and supplies the read information to the system controller 32.

The system controller 32 counts the number of times the car changes its orientation based on the orientation information supplied from the geomagnetic sensor 31, and stores the counted value into an orientation/speed change count memory 37. The system controller 32 also counts the number of times the car is accelerated or decelerated based on the running speed information supplied from the speed/ running distance measuring unit 35, and stores the counted value into the orientation/speed change count memory 37. Further, the system controller 32 calculates the coordinates of the current location of the car on the map based on the orientation, latitude and longitude information supplied from the geomagnetic sensor 31 and the GPS unit 33, and supplies a display unit 38 with a composite video signal including a video signal for displaying a mark indicative of its own location on the current location coordinates and a video signal corresponding to the reproduced map information. The system controller 32 further determines a road on which the car is currently running (hereinafter called "the current running road") based on the current location coordinates and reproduced map information. In this event, the system controller 32 retrieves road information corresponding to the running road determined as described above from the road information supplied from the CD-ROM player 36, and sends the retrieved road information to the CPU bus 100 as currently running road information. For example, such road information may be identification information for distinguishing superhighways from ordinary roads. If the road on which the car is currently running is determined to be a superhighway, the system controller 32 sends the currently running road information set to logical "1" to the CPU bus 100. On the other hand, if the currently running road is determined to be an ordinary road, the system controller 32 sends the currently running road information set to logical "0" to the CPU bus 100.

Further, the system controller 32 reads the orientation change count information and the speed change count information stored in the orientation/speed change count memory 37 in response to a variety of read command signals supplied thereto from the CPU bus 100, and sends the read information to the CPU bus 100. Furthermore, the system controller 32 sends the current time information and the accumulated running distance information to the CPU bus 100 in response to a variety of read command signals supplied thereto from the CPU bus 100. The display unit 38 displays an image based on a video signal supplied thereto.

An alarm sound generator unit 4 in FIG. 1 outputs an audible alarm message in response to an alarm sound command signal supplied thereto through the CPU bus 100.

The display unit 5 displays an alarm message in response to an alarm display command signal supplied thereto through the CPU bus 100. A fragrance generator unit 6 diffuses stimulative fragrance into the car in response to a fragrance generation command signal supplied thereto through the CPU bus 100. A sleepy time zone setting switch 7 generates a sleepy time zone setting signal in response to the driver's manipulation to the switch 7 and sends this signal to the CPU bus 100. The driver pushes the sleepy time zone setting switch 7 when he himself is conscious of sleepiness. An minor tremor (MT) pickup 8 is mounted on a belt attached to a driver's seat for detecting tremors on the driver's skin in the range of 1 to 10 millimeters, which may occur on the surface of the skin, and supplies a skin tremor signal corresponding to the detected skin tremors to a cardiac rate detector circuit 9.

Figure 3:
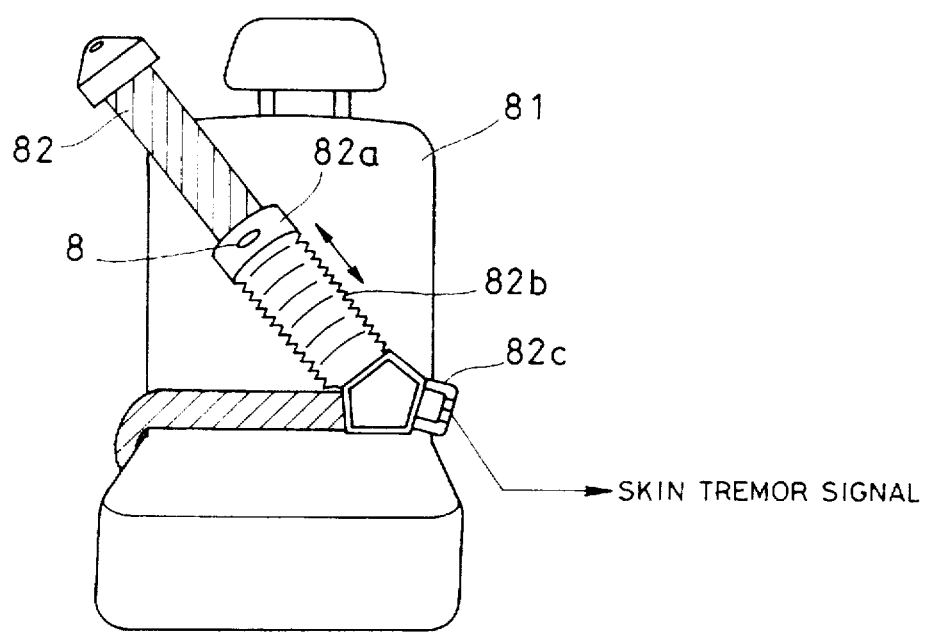
FIG. 3 shows an example depicting how an MT pickup 8 of the cardiac rate measuring apparatus according to the present invention is attached.

FIG. 3 shows an example depicting how the MT pickup 8 is mounted on a seat belt.

Referring specifically to FIG. 3, a pickup fixing ring 82a is movably fit on a seat belt 82 attached to a driver's seat 81. The MT pickup 8 is mounted on the pickup fixing ring 82a. A transmission cable for transmitting the skin tremor signal generated by the MT pickup 8 is connected to a seat belt buckle 82c through a telescopic bellows member 82b wrapped around the seat belt 82. Stated another way, the skin tremor signal output from the MT pickup 8 is supplied to the cardiac rate detector circuit 9 through the seat belt buckle 82c.

The driver, when fastening the seat belt 82, adjusts the position of the pickup fixing ring 82a so as to locate a skin tremor detecting surface of the MT pickup 8 in contact with the driver. It should be noted that the MT pickup 8 need not be in direct contact with the driver's body. That is, the skin tremor detecting surface of the MT pickup 8 may only be brought into contact with the driver through his clothes and the seat belt 82.

The cardiac rate detector circuit 9 generates a cardiac rate signal corresponding to the cardiac rate of the driver based on the supplied skin tremor signal, and sends the cardiac rate signal to the CPU bus 100.

FIG. 4 shows the internal configuration of the cardiac rate detector circuit 9, and FIGS. 5a–5e show waveforms (a–e) of signals output from respective constituent modules of the cardiac rate detector circuit 9.

Referring specifically to FIG. 4, an amplifier 91 amplifies the supplied skin tremor signal having high frequency noise components removed therefrom to a desired signal level, and supplies the amplified skin tremor signal a to a band pass filter (BPF) 92. The BPF 92, which is a band pass filter designed to pass 10 Hz components of the amplified skin tremor signal a, supplies a filtered skin tremor signal b to a peak hold circuit 93.

Figure 6:
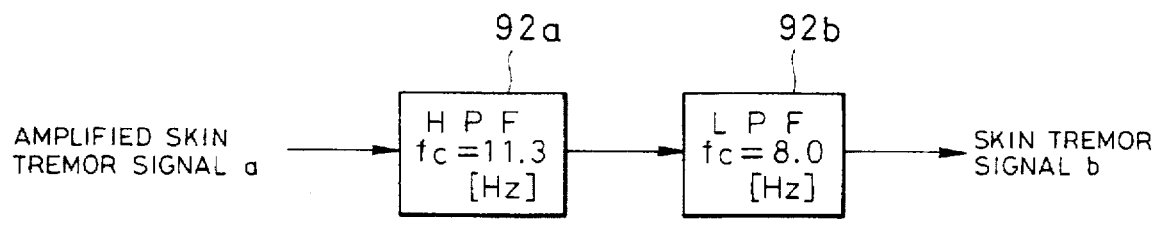
FIG. 6 is a diagram showing an exemplary internal configuration of a band pass filter 92.

FIG. 6 shows an example of the internal configuration of the BPF 92 as described above.

Figure 7:
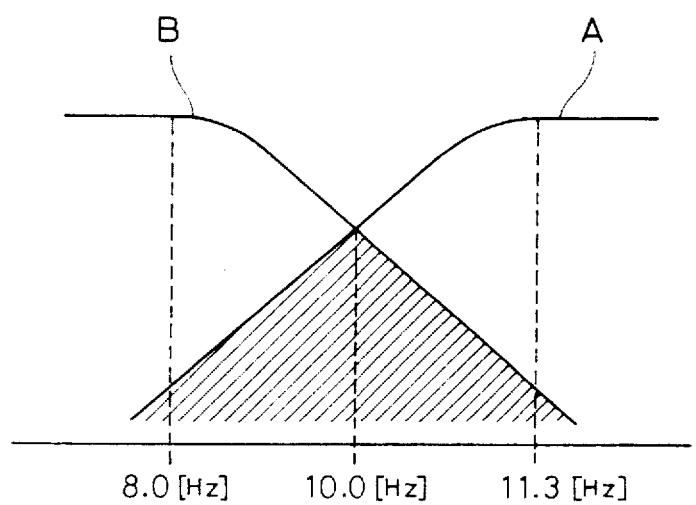
FIG. 7 is a graph showing the cut-off characteristics of a high pass filter 92a and a low pass filter 92b.

In FIG. 6, a high pass filter (HPF) 92a is designed to have a cut-off frequency fc at 11.3 Hz. The cut-off characteristic of the HPF 92a is indicated by a solid line A in FIG. 7. A low pass filter (LPF) 92b is designed to have a cut-off frequency fc at 8.0 Hz. The cut-off characteristic of the LPF 92b is indicated by a solid line B in FIG. 7. The BPF 92 configured as shown in FIG. 6 allows the filtered skin tremor signal b composed of frequency band components indicated by a hatched area in FIG. 7 to be supplied to the peak hold circuit 93.

The peak hold circuit 93 generates an envelope waveform by holding respective level peak values of the skin tremor signal b as a cardiac rate signal c. The time constant for the peak hold operation is set, for example, to 0.1 seconds. A low pass filter (LPF) 94 filters out noise components mixed in the cardiac rate signal c to generate a cardiac rate signal d which is supplied to an analog-to-digital (A/D) convertor 95. The cut-off frequency fc of the LPF 94 is, for example, 5.3 Hz. The A/D convertor 95 samples the cardiac rate signal d at a predetermined sampling timing to generate a digital cardiac rate signal e which is then sent to the CPU bus 100.

More specifically, being that a signal corresponding to a cardiac rate is mixed in approximately 10 Hz components of the skin tremor signal, the cardiac rate detector circuit 9 extracts components near 10 Hz from the skin tremor signal, and holds peak levels of the extracted signal to generate an envelope waveform signal as a cardiac rate signal corresponding to the cardiac rate of the driver.

It should be noted that the cut-off frequency of the LPF 94 is selected to be 5.3 Hz which is rather low as compared with the frequency of the desired signal at approximately 10 Hz extracted from the skin tremor signal, because the LPF 94 is composed of analog circuits and has a gently sloping cut-off characteristics so that a bit of the desired 10 Hz components are also attenuated. The value of the cut-off frequency for the LPF 94, however, is selected in order to provide larger effects of removing noise components, which is given a higher priority. It should be noted that the cut-off frequency of the LPF 94 may be any value as long as the LPF 94 passes desired frequency components therethrough and effectively removes noise components.

Figure 8:
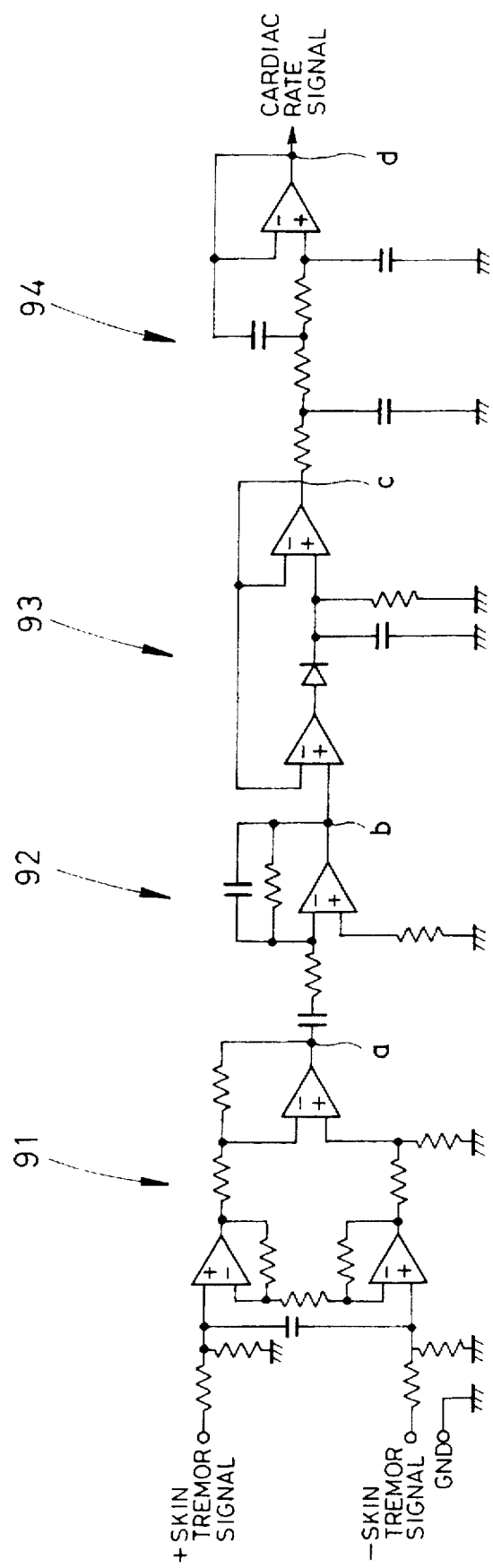
FIG. 8 is a diagram showing an exemplary circuit configuration of the cardiac rate detector circuit 9.

FIG. 8 shows an example of the circuit configuration for realizing the cardiac rate detector circuit 9 as shown in FIG. 4.

As described above, the cardiac rate measuring apparatus of the present invention comprising the MT pickup 8 and the cardiac rate detector circuit 9 is designed to detect tremors occurring on the surface of the driver's skin ranging from one to ten microns through clothes of the driver and the seat belt 82, and hold level peak values of the skin tremor signal corresponding to the skin tremors to generate an envelope waveform signal which is used as the cardiac rate signal corresponding to the cardiac rate of the driver. Thus, the cardiac rate measuring apparatus can measure the cardiac rate of the driver without directly attaching cardiac rate detecting electrodes on the breast or on the tips of driver's fingers.

Referring again to FIG. 1, a digital signal processor (DSP) 10 performs Fast Fourier Transformation (FFT) on an RR signal supplied thereto through the CPU bus 100 and measures components at 0.05 to 0.15 Hz and components at 0.15 to 0.4 Hz of the RR signal, respectively. The DSP 10 sends the components at 0.05–0.15 Hz as a Mayer Wave related sinus arrhythmia (MWSA) value and the components at 0.15 to 0.4 Hz as a respiration sinus arrhythmia (RSA) value to the CPU bus 100.

Figure 5A:
FIG. 5a–5e show waveforms of signals output from respective constituent modules of the cardiac rate detector circuit 9.
Figure 5B:
Figure 5C:
Figure 5D:
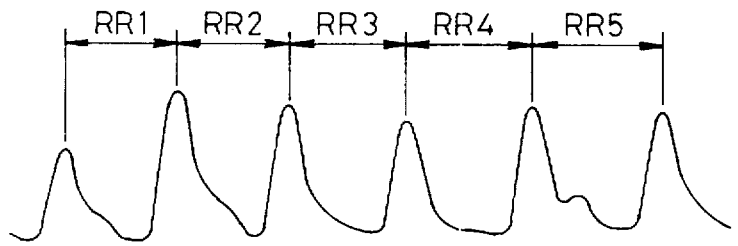

The above-mentioned RR signal is composed of respective heartbeat intervals of the cardiac rate arranged in time series. For example, heartbeat intervals RR1–RR5 of the cardiac rate signal d as shown in FIG. 5d are time-serially arranged to generate the RR signal. The MWSA value indicates fluctuations in the heartbeat intervals relative to respiratory motions, and is known to be utilized as an activity index for the sympathetic nerve system. The RSA value, in turn, indicates fluctuations in the heartbeat intervals relative to fluctuations in blood pressure, and is known to be utilized as an activity index for the parasympathetic nerve system.

Figure 9:
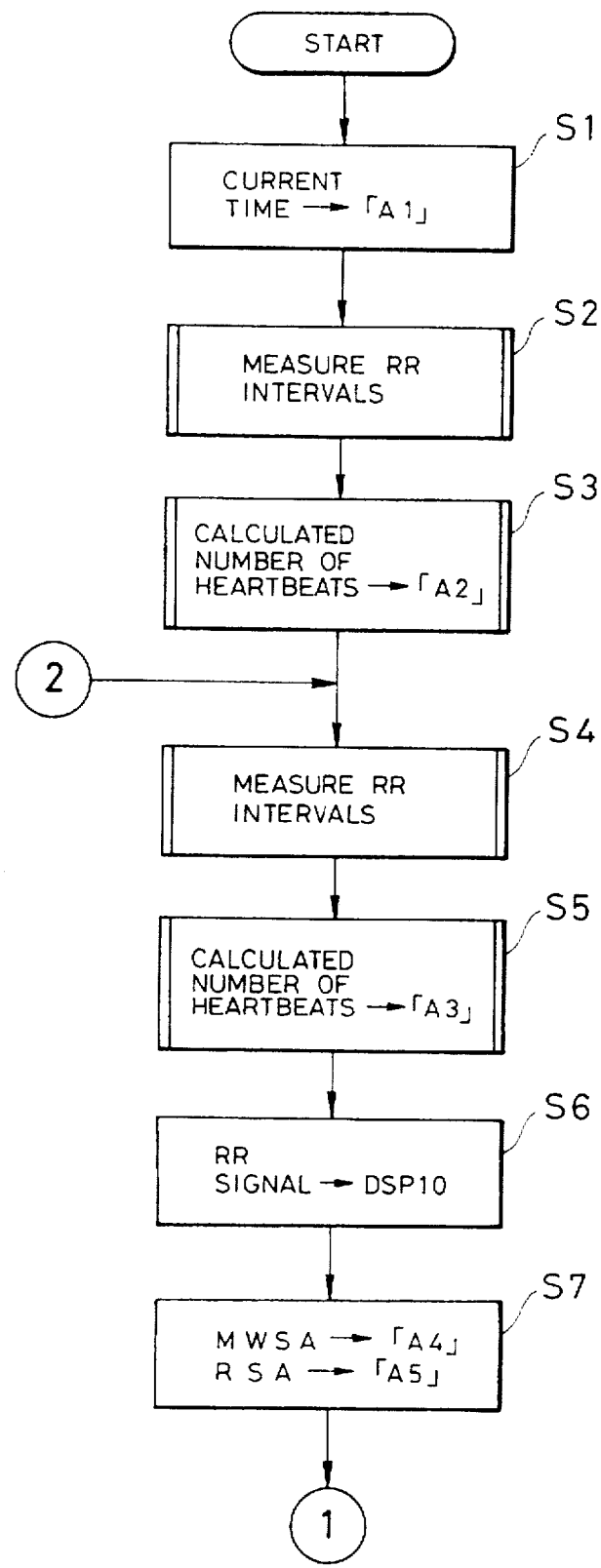
FIGS. 9 and 10 are flow charts representing a main routine of a driver's mental condition detection.
Figure 10:
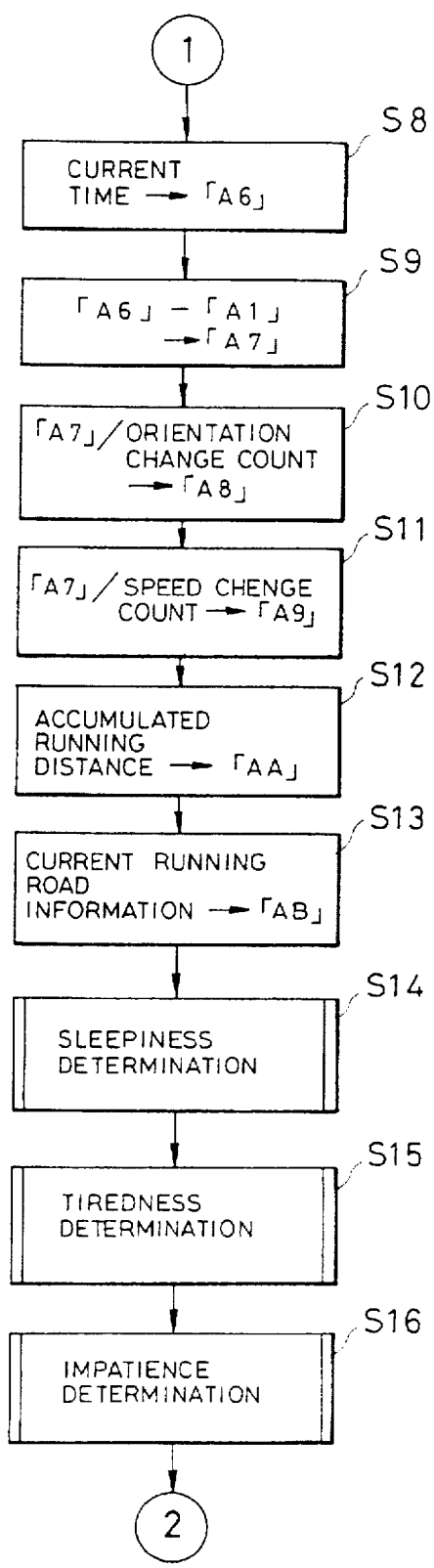

A central processing unit (CPU) 11 reads a variety of signals, as described above, sent onto the CPU bus 100 in accordance with a driver's mental condition detecting procedure stored in a read only memory (ROM) 12, and sends a variety of command signals to the CPU bus 100. A random access memory (RAM) 13 stores a variety of information intermediately generated during the execution of the driver's mental condition detecting procedure. FIGS. 9 and 10 shows a main flow of the driver's mental condition detection executed by the CPU 11 in response to the start-up of the engine of the car. FIG. 11 shows a memory map for the RAM 13 for storing a variety of information intermediately generated during the execution of the main flow.

Figure 5E:
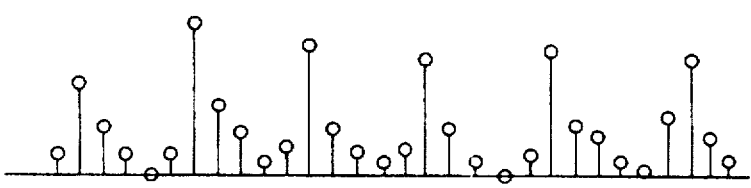

First, the CPU 11 reads current time information from the navigation system 3, and stores the current time information as a starting time Ts into RAM 13 at "A1" address (step S1). Next, the CPU 11 proceeds to the execution of an RR measuring subroutine for measuring the heartbeat intervals RR of a cardiac rate signal (step S2). In the RR measuring subroutine, the CPU 11 measures respective heartbeat intervals RR of the cardiac rate signal for a predetermined time period based on respective sample values of the digital cardiac rate signal e as shown in FIG. 5e, supplied from the cardiac rate detector circuit 9, and sequentially stores them into respective storing locations in the RAM 13 from a "C1" address. For example, the CPU 11 first detects, in order, turning points at which the sampling values of the digital cardiac rate signal e as shown in FIG. 5e transit from an increasing trend to a decreasing trend. A turning point detected time is determined to be a signal peak timing if the sampling values of the digital cardiac rate signal e do not transit to the increasing trend for 0.5 seconds from the turning point detected time. Next, the CPU 11 determines a time interval between adjacent signal peak timings as the heartbeat interval RR and sequentially stores them into storing locations in the RAM 13 from the "C1" address.

After the execution of the RR measuring subroutine, the CPU 11 proceeds to the execution of a heartbeat number calculating subroutine for calculating the number of heartbeats (step S3). In the heartbeat number calculating subroutine, the CPU 11 calculates the number of heartbeats per unit time based on the heartbeat intervals RR stored in the respective storing locations in the RAM 13 from the "C1" address, and stores the number of heartbeats as an initial number of heartbeats HRs into the RAM 13 at "A2" address. In this event, the total number of samples of the heartbeat intervals RR stored at "C1" and subsequent addresses in the RAM 13 is divided by a total heartbeat interval value calculated by adding the respective values of the heartbeat intervals RR to derive a number of heartbeats per unit time. After completing the execution of the heartbeat number calculating subroutine, the CPU 11 proceeds to the execution of the RR measuring subroutine for measuring the heartbeat intervals RR of the cardiac rate signal (step S4). Since the RR measuring subroutine at step S4 is the same as that executed at the foregoing step S2, its detailed explanation will be omitted.

After completing the execution of the RR measuring subroutine at step S4, the CPU 11 proceeds to the execution of a heartbeat number calculating subroutine for calculating the number of heartbeats (step S5). In the heartbeat number calculating subroutine, the CPU 11 calculates the number of heartbeats per unit time based on the heartbeat intervals RR stored in the respective storing locations in the RAM 13 from the "C1" address, and stores this number of heartbeats as a current number HR of heartbeats into the RAM 13 at "A3" address. After completing the execution of the heartbeat number calculating subroutine at step S5, the CPU 11 sequentially reads the heartbeat intervals RR stored in the respective storing locations in the RAM 13 from the "C1" address, and transfers the read values as the RR signal to the DSP 10 (step S6). By the execution of the step S6, the DSP 10 performs the FFT processing on the RR signal to extract components at 0.05–0.15 Hz of the RR signal as the MWSA value and components at 0.15–0.4 Hz of the RR signal as the RSA value, both of which are sent to the CPU bus 100. The CPU 11 fetches these MWSA value and RSA value and stores the MWSA value into the RAM 13 at "A4" address, and the RSA value into the RAM 13 at "A5" address (step S7).

Next, the CPU 11 reads the current time information from the navigation system 3, and stores the read current time information as a current time T into the RAM 13 at "A6" address (step S8). Then, the CPU 11 read the starting time Ts from "A6" address in the RAM 13, and subtracts the starting time Ts from the current time T to derive a continuous driving time S which is stored into the RAM 13 at "A7" address (step S9). The CPU 11 next reads the car orientation change count information from the navigation system 3, and divides the read car orientation change count information by the continuous driving time S stored at "A7" address in the RAM 13, and stores the inverse of the quotient into the RAM 13 at "A8" address as an orientation variance parameter $1/\sigma a$ (step S10). The CPU 11 next reads the car speed change count information from the navigation system 3, divides the read car speed change count information by the continuous driving time S stored at "A7" address in the RAM 13, and stores the inverse of the quotient as a speed variance parameter $1/\sigma u$ into the RAM 13 at "A9" address (step S11).

The CPU 11 next reads the accumulated running distance information from the navigation system 3, and stores the read accumulated running distance information into the RAM 13 at "A" address as a traveling distance L (step S12). Then, the CPU 11 reads the current running road information from the navigation system 3, and stores the read current running road information into the RAM 13 at "AB" address as current running road information D (step S13). After completing step S13, the CPU 11 proceeds to a sleepiness determining subroutine (step S14).

Figure 12:
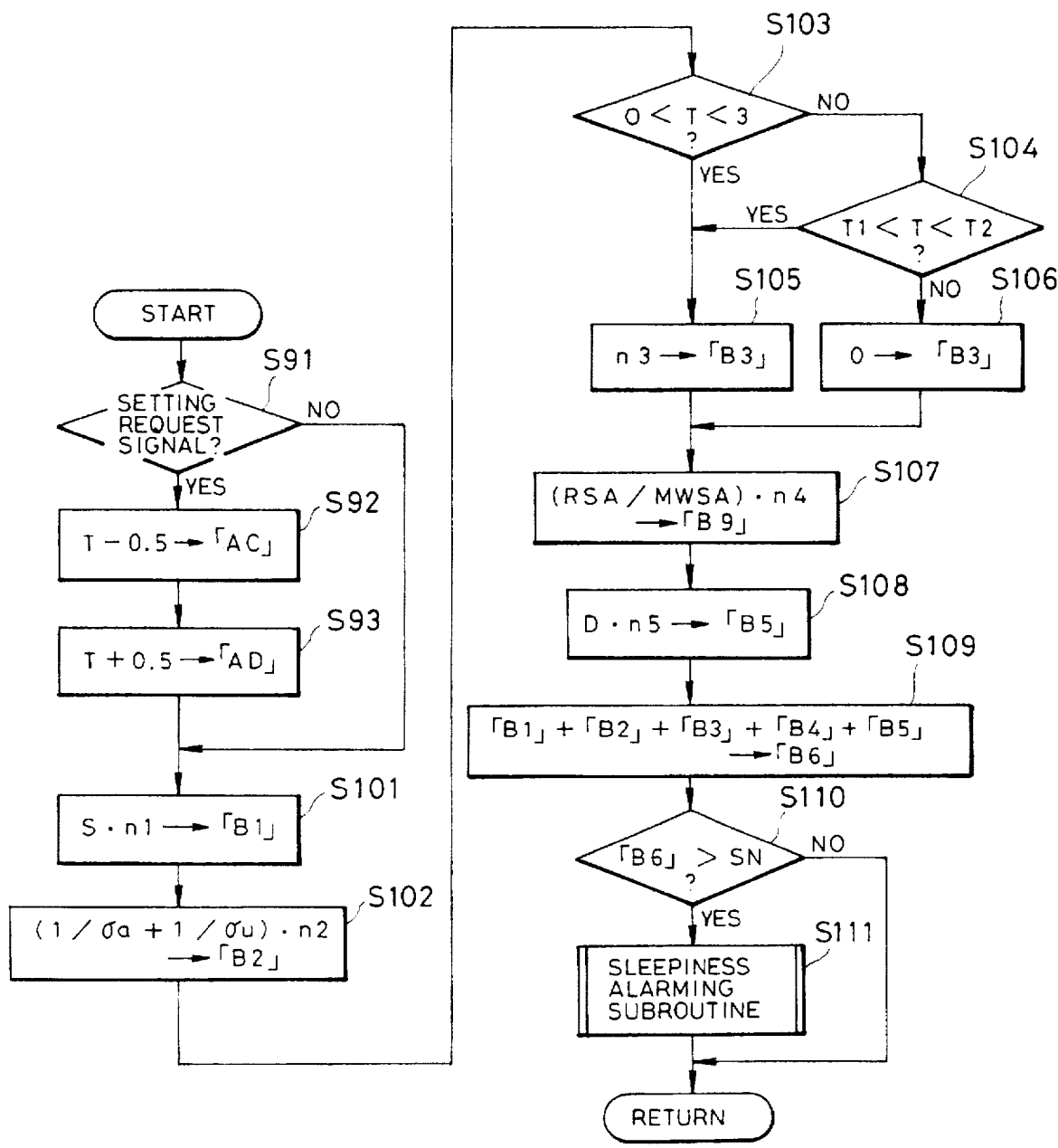
FIG. 12 is a flow chart representing a sleepiness determining subroutine.

FIG. 12 is a flow chart representing the sleepiness determining subroutine.

Referring specifically to FIG. 12, the CPU 11 first determines whether or not a sleepy time zone setting request signal has been sent from the sleepy time zone setting switch 7 (step S91). If determining at step S91 that the sleepy time zone setting request signal has been sent, the CPU 11 reads the current time T stored at "A6" address in the RAM 13, subtracts 0.5 hours from the current time T, and stores the resulting value into the RAM 13 at "AC" address as a sleepiness occurring time T1 (step S92). The CPU 11 next adds 0.5 hours to the current time T, and stores the resulting time information into the RAM 13 at "AD" address as a sleepiness occurring time T2 (step S93). After the completion of step S93 or if the CPU 11 determines at step S91 that the sleepy time zone setting request signal has not been sent, the CPU 11 reads the continuous driving time S stored at "A7" address in the RAM 13, and multiplies the continuous driving time S by a sleepiness determining coefficient n1, and stores the product S·n1 into the RAM 13 at "B1" address as a sleepiness determining parameter based on a driving lapse time (step S101).

The CPU 11 next stores the orientation variance parameter $1/\sigma a$ stored at "A8" address in the RAM 13 and the speed variance parameter $1/\sigma u$ stored at "A9" address in the RAM 13, adds them to each other, and multiplies the sum by a sleepiness determining coefficient n2, and stores the product $(1/\sigma a+1/\sigma u)\cdot n2$ into the RAM 13 at "B2" address as a sleepiness determining parameter based on the monotonous driving (step S102). The CPU 11 then reads the current time T stored at "A6" address in the RAM 14, and determines whether the current time T indicates the time between 0 AM and 5 AM or between 1 PM and 3 PM (step S103). Determining at step S103 that the current time T is not between 0 AM and 5 AM or between 1 PM and 3 PM, the CPU 11 reads the sleepiness occurring times T1 and T2 stored at "AC" and "AD" addresses in the RAM 13, respectively, and determines whether or not the current time T is the time between the sleepiness occurring times T1 and T2 (step S104).

If the CPU determines at step S103 that the current time T is between 0 AM and 5 AM or between 1 PM and 3 PM, or determines at step S104 that the current time T is between the sleepiness occurring times T1 and T2, the CPU 11 stores a sleepiness determining coefficient n3 into the RAM 13 at "B3" address as a sleepiness determining parameter based on a driving time zone (step S105). On the other hand, determining at step S104 that the current time T is not the time between the sleepiness occurring times T1 and T2, the CPU 11 stores zero into the RAM 13 at "B3" address (step S106). After completing steps S105 or S106, the CPU 11 reads the MWSA value stored at "A4" address in the RAM 13 and the RSA value stored at "A5" address in the RAM 13, divides the RSA value by the MWSA value, multiplies the quotient by a sleepiness determining coefficient n4, and stores the product (RSA/MWSA)·n4 into the RAM 13 at "B4" address as a sleepiness determining parameter based on the automatic nerve system (step S107).

The CPU 11 next read the current running road information D stored at "AB" address in the RAM 13, multiplies the current running road information D by the sleepiness determining coefficient n5, and stores the product D·n5 into the RAM 13 at "B5" address as a sleepiness determining parameter based on a running road situation (step S108). Subsequently, the CPU 11 adds each of the sleepiness determining parameters stored at "B1"–"B5" addresses in the RAM 13 to generate a sleepiness determining value Pn which is stored into the RAM 13 at "B6" address (step S109). More specifically, by executing step S109, the sleepiness determining value Pn expressed by:

Pn=S·En1+(1/σa+1/σu)·En2+n3+(RSA/MWSA)·En4+ D·En5; or

Pn=S·En1+(1/σa+1/σu)·En2+(RSA/MWSA)·En4+D·En5 is stored into the RAM 13 at "B6" address.

The CPU 11 next determines whether or not the sleepiness determining value Pn stored at "B6" address in the RAM 13 is a larger value than a sleepiness threshold SN (step S110). Determining at step S110 that the sleepiness determining value Pn is a value larger than the sleepiness determining threshold SN, the CPU 11 proceeds to the execution of a sleepiness alarming subroutine (step S111).

In the sleepiness alarming subroutine, the CPU 11 supplies the CD player in the audio system 1 with a play start command signal as well as with a high speed play command signal for increasing the playing speed of the CD player. Further, the CPU 11 supplies the amplifier in the audio system 1 with a volume increase command signal for increasing the volume of sound generated from the audio system 1. Furthermore, the CPU 11 supplies the equalizer in the audio system 1 with a treble and bass increase command signal for increasing treble and bass components. A sequence of these operations causes sound to be output with increased volume and with emphasized high and low in the sleepiness alarming subroutine, the CPU 11 supplies the air-conditioning system 2 with an internal temperature decrease command signal. The air-conditioning system 2, in response to the internal temperature decrease command signal, supplies cooling air in order to decrease the internal temperature lower by a predetermined value than a current internal temperature. In this event, the air-conditioning system 2 adjusts the direction of the blower hole such that the driver is directly exposed to the cooling air. Also, in the sleepiness alarming subroutine, the CPU 11 supplies a sleepiness alarm command signal to the alarm sound generator unit 4 and the display unit 5, respectively. In response to the sleepiness alarm command signal, the alarm sound generator unit 4 audibly outputs a message for alarming the driver that he is sleepy. The display unit 5, on the other hand, displays a message for alarming the driver that he is sleepy in response to the sleepiness alarm command signal. In the sleepiness alarming subroutine, the CPU 11 also supplies a fragrance generation command signal to the fragrance generator unit 6. The fragrance generator unit 6, in response to the fragrance generation command signal, diffuses stimulative fragrance into the car.

In summary, the sleepiness determining subroutine shown in FIG. 12 utilizes the continuous driving time, monotonous driving, driving time zone, and automatic nerve condition of the driver to totally determine whether or not the driver feels sleepiness.

For example, when the driver has been continuously driving a car for a long time, i.e., when the value $S\beta n1$ calculated at step S101 presents a larger value, it may be determined that the driver feels sleepiness with a higher probability. Also, with less number of times the driver has changed the orientation of the car and accelerated the car per unit time, resulting in monotonous driving, i.e., when the value $(1/\sigma a+1/\sigma u) \cdot n2$ calculated at step S102 presents a larger value, it may be determined that the driver feels sleepiness with a higher probability. Further, the driver will feel sleepiness with a higher probability when he is driving in midnight. In the foregoing embodiment, when a driving time zone is between 0 AM and 5 AM or between 1 PM and 3 PM, the sleepiness determining coefficient n3 is added as a sleepiness determining parameter. It should be noted that in the foregoing embodiment, even outside of the time zones between 0 AM and 5 AM and between 1 PM and 3 PM, if the driver himself, conscious of his sleepiness, pushes the sleepy time zone setting switch 7, a time zone including 0.5 hours before and after the sleepy time zone setting switch 7 is pushed is stored as a sleepy time zone (steps S91–S93). Thus, the sleepiness determining coefficient n3 is added as the sleepiness determining parameter only when the driver drives a car during the time zones between 0 AM and 5 AM and between 1 PM and 3 PM or during a sleepy time zone set by the driver as described above (steps S103–S106).

As the RSA value as an activity index for the parasympathetic nerve system is larger while the MWSA value as an activity index for the sympathetic nerve system is smaller, it may be determined that the driver is sleepy with a higher possibility. Thus, when the driver is sleepy, the value (RSA/MWSA)·n4 calculated at step S107 becomes larger.

When running on a superhighway, instantaneous sleepiness would result in an accident with a higher possibility as compared with running on an ordinary road. To cope with this situation, in the foregoing embodiment, the current running road information D indicative of whether or not the car is currently running on a superhighway is multiplied by the sleepiness determining coefficient n5, and the product is added as a sleepiness determining parameter. Specifically, since the current running road information D is set to logical "1" when the car is currently running on a superhighway and to logical "0" when running on an ordinary road, the sleepiness determining coefficient n5 is added as a sleepiness determining parameter only when the car is currently running on a superhighway as a result. While the foregoing embodiment adds the sleepiness determining coefficient n5 as a sleepiness determining parameter depending on whether the car is currently running on an ordinary road or on a superhighway, the present invention is not limited to this configuration. Alternatively, the CPU 11 may read information indicating whether or not the car is approaching to an accident frequently happening location as the current running road information D, by way of example, and a sleepiness determining coefficient n6 may be added as a sleepiness determining parameter only when the current running road is directing the car to such an accident frequently happening location. In the sleepiness determining subroutine as described above, a sleepiness alarm is finally generated (step S111) if the sleepiness determining value Pn, which is the sum of the respective sleepiness determining parameters, is larger than the predetermined sleepiness determining threshold SN (steps S109 and S110), determining that the driver is sleepy.

After the completion of the sleepiness alarming subroutine at step S111, or if the sleepiness determining value Pn stored at "B6" address in the RAM 13 is not larger than the sleepiness determining threshold SN, the CPU 11 returns to the main flow as shown in FIG. 10 and proceeds to the execution of a tiredness determining subroutine (step S15).

Figure 13:
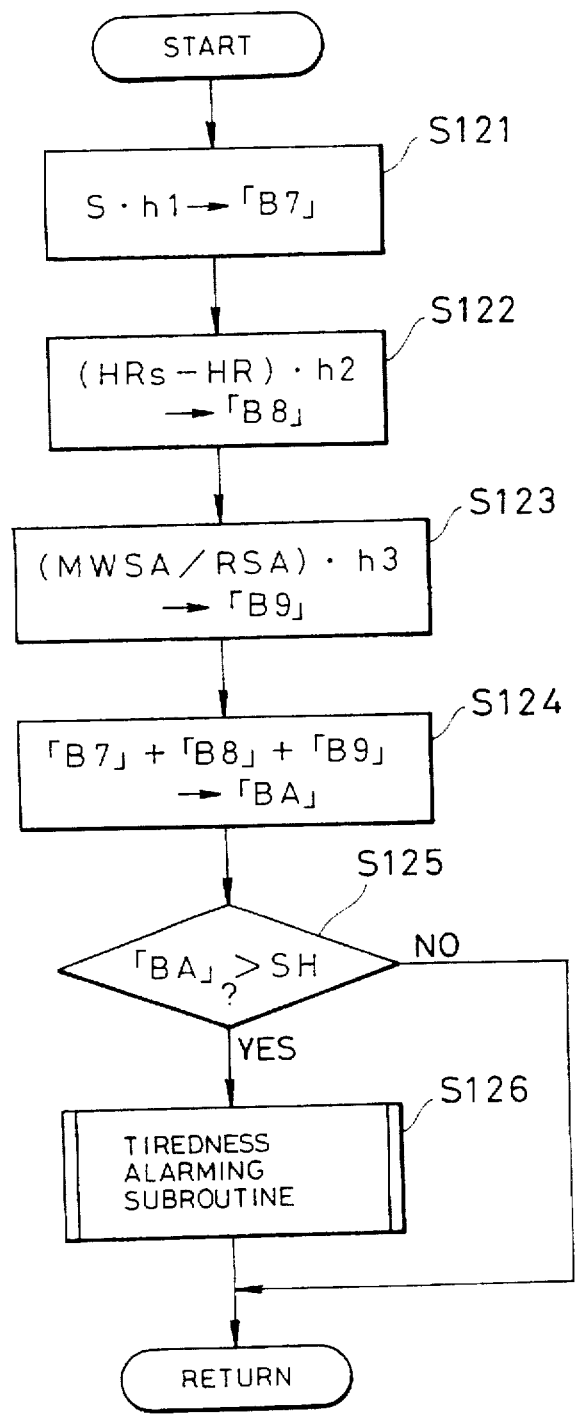
FIG. 13 is a flow chart representing a tiredness determining subroutine.

FIG. 13 shows a flow chart representing the tiredness determining subroutine.

Referring specifically to FIG. 13, the CPU 11 first reads the continuous driving time S stored at "A7" address in the RAM 13, multiplies the continuous driving time S by a tiredness determining coefficient h1, and stores the product S·h1 into the RAM 13 at "B7" address as a tiredness determining parameter based on the driving time (step S121).

The CPU 11 next reads the initial heartbeat number HRs stored at "A2" address in the RAM 13 and the current heartbeat number HR stored at "A3" address in the RAM 13, subtracts Hr from Hrs, multiplies the difference by a tiredness determining coefficient h2, and stores the product (HRs-HR)·h2 into the RAM 13 at "B8" address as a tiredness determining parameter based on changes in the number of heartbeats (step S122).

Then, the CPU 11 reads the MWSA value stored at "A4" address in the RAM 13 and the RSA value stored at "A5" address in the RAM 13, divides the MWSA value by the RSA value, multiplies the quotient by a tiredness determining coefficient h3, and stores the product (MWSA/RSA)·h3 into the RAM 13 at "B9" address as a tiredness determining parameter based on the automatic nerve system (step S123).

Subsequently, the CPU 11 adds the respective tiredness determining parameters stored at "B7"–"B9" addresses in the RAM 13 to generate a tiredness determining value Ph which is stored into the RAM 13 at "BA" address (step S124). By executing step S124, the tiredness determining value Ph expressed by:

$$Ph = S \cdot h1 + (HRs-HR) \cdot h2 + (MWSA/RSA) \cdot h3$$ is stored into the RAM 13 at "BA" address.

The CPU 11 next determines whether the tiredness determining value Ph stored at "BA" address in the RAM 13 has a lager value than a tiredness determining threshold SH (step S125). Determining at step S125 that the tiredness determining value Ph is larger than the tiredness determining threshold SH, the CPU 11 proceeds to the execution of a tiredness alarming subroutine (step S126).

In the tiredness alarming subroutine, the CPU 11 supplies the CD player in the audio system 1 with a play start command signal as well as with a high speed play command signal for increasing the playing speed of the CD player. The CPU 11 further supplies the amplifier in the audio system 1 with a volume increase command signal for increasing the volume of sound generated by the audio system 1. Furthermore, the CPU 11 supplies the equalizer in the audio system 1 with a treble and bass increase command signal for increasing treble and bass components. A sequence of these operations cause sound to be output with larger volume and with emphasized treble and bass at a play speed higher than usual.

Also, in the tiredness alarming subroutine, the CPU 11 supplies a tiredness alarm command signal to the alarm sound generator unit 4 and the display unit 5, respectively. In response to the tiredness alarm command signal, the alarm sound generator unit 4 audibly outputs a message for animating the driver. For example, the alarm sound generator unit 4 audibly outputs a message for promoting the driver to take moderate exercises in response to the tiredness alarm command signal.

In summary, the tiredness determining subroutine shown in FIG. 13 utilizes the continuous driving time, changes in the number of heartbeats of the driver, and automatic nerve condition of the driver as parameters for determining the tiredness, and totally determines based on all these parameters whether or not the driver is tired.

For example, if the driver has been driving for a long time, i.e., if the value S·h1 calculated at step S121 is larger, it may be determined that the driver is tired with a higher probability. Also, if the number of heartbeats is decreasing, i.e., if the value (HRs−HR)·h2 calculated at step S122 is larger, it may be determined that the driver is tired with a higher possibility. Further, as the RSA value as an activity index for the parasympathetic nerve system is smaller while the MWSA value as an activity index for the sympathetic nerve system is larger, i.e., if the value (RSA/MWSA)·h4 calculated at step S123 is larger, it may be determined that the driver is tired with a higher possibility. The tiredness determining subroutine finally determines that the driver is tired and generates a tiredness alarm (step S126), when the tiredness determining value Ph, which is the sum of the tiredness determining parameters, is larger than the predetermined tiredness determining threshold SH (steps S124 and S125).

Figure 14:
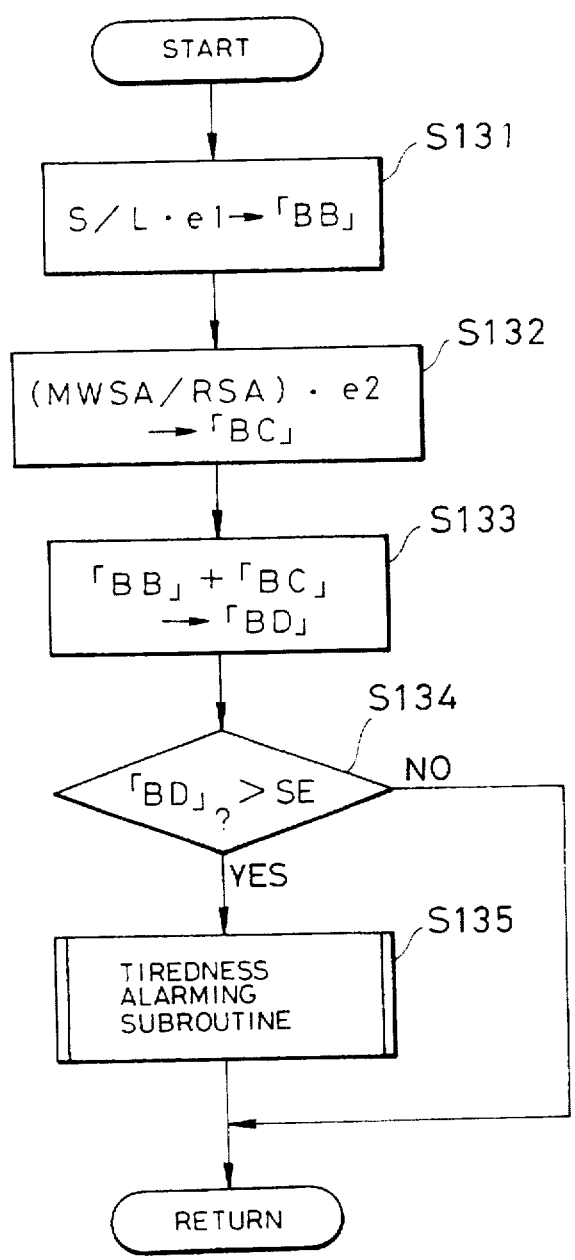
FIG. 14 is a flow chart showing an impatience determining subroutine.

After completing the tiredness alarming subroutine at step S126, or if the CPU 11 determines that the tiredness determining value Ph stored at "BA" address in the RAM 13 is not larger than the tiredness determining threshold SH, the CPU 11 returns to the main flow shown in FIG. 10, and proceeds to the execution of the next impatience determining subroutine (step S16). FIG. 14 shows a flow chart representing the impatience determining subroutine.

Referring specifically to FIG. 14, the CPU 11 first reads the continuous driving time S stored at "A7" address in the RAM 13 and a travelling distance L stored at "AA" address in the RAM 13, and divides the continuous driving time S by the travelling distance L to derive an inverse of a travelling distance per unit time. Further, the CPU 11 multiplies the inverse of the travelling distance per unit time by an impatience determining coefficient e1, and stores the product (S/L)·e1 into the RAM 13 at "BB" address as an impatience determining parameter based on the travelling distance per unit time (step S131). Next, the CPU 11 reads the MWSA value stored at "A4" address in the RAM 13 and the RSA value stored at "A5" in the RAM 13, divides the MWSA value by the RSA value, multiplies the quotient by an impatience determining coefficient e2 to drive a value (MWSA/RSA)·e2 which is stored into the RAM 13 at "BC" address as an impatience determining parameter based on the automatic nerve system (step S132).

Next, the CPU adds the respective impatience determining parameters stored at the "BB" and "BC" addresses in the RAM 13 as described above to derive an impatience determining value Pe which is stored into the RAM 13 at "BD" address (step S133). Stated another way, the execution of the step S133 causes the impatience determining value Pe expressed by:

Pe=(S/L)·e1+(MWSA+RSA)·e2 to be stored into the RAM 13 at the "BD" address.

The CPU 11 next determines whether or not the impatience determining value Pe stored at the "BD" address in the RAM 13 is larger than an impatience determining threshold SE (step 134). Determining at step S134 that the impatience determining value Pe is larger than the impatience determining threshold SE, the CPU 11 proceeds to the execution of an impatience alarming subroutine (step S135).

In the impatience alarming subroutine, the CPU 11 supplies the CD player in the audio system 1 with a low speed play command signal for decreasing the play speed of the CD player. The CPU 11 also supplies the amplifier in the audio system 1 with a volume decrease command signal for decreasing the volume of sound generated by the audio system 1. Furthermore, the CPU 11 supplies the equalizer in the audio system 1 with a treble and bass decrease command signal for decreasing treble and bass components. A sequence of these operations causes reproduced music to be output with lower volume at a play speed lower than usual.

In the impatience alarming subroutine, the CPU 11 also supplies an impatience alarm command signal to the alarm sound generator unit 4 and the display unit 5. The alarm sound generator unit 4, in response to the patience alarm command signal, audibly outputs a message for calming down the driver. For example, the alarm sound generator unit 4 audibly generates a message for promoting the driver to breathe deeply in response to the impatience alarm command signal. In the impatience alarming subroutine, the CPU 11 further supplies a fragrance generation command signal to the fragrance generator unit 6. In this event, the fragrance generator unit 6 diffuses fragrance which may hold driver's excitement into the car.

In summary, the impatience determining subroutine shown in FIG. 14 utilizes the inverse number of the travelling distance of the car per unit time and an automatic nerve system condition of the driver as parameters for determining impatience of the driver, and totally determines whether or not the driver is impatient.

For example, if the inverse number of the travelling distance of the car per unit time, i.e., the value (S/L)·e1 calculated at the foregoing step S131 is larger, it may be determined that the driver is increasingly impatient with a higher probability. Also, as the RSA value as an activity index for the parasympathetic nerve system is smaller while the MWSA value as an activity index for the sympathetic nerve system is larger, i.e., if the value (MWSA/RSA)·e2 calculated at the foregoing step S132 is larger, it may be determined that the driver is impatient with a high possibility.

In the impatience determining subroutine, if the impatience determining value Pe, which is the sum of the respective impatience determining parameters, is larger than the predetermined impatience determining threshold SE (steps S133 and S134), an impatience alarm is generated, determining that the driver is impatient (step S135).

After the completion of the impatience alarming subroutine at step S135, or if the CPU 11 determines at step S134 that the impatience determining value Pe stored at "BD" address in the RAM 13 is not larger than the impatience determining threshold SE, the CPU 11 returns to step S4 in the main flow shown in FIG. 9 to repetitively execute the operations hereinbefore described.

As described above, in the detection of driver's mental conditions, a variety of physiological data on the driver driving a car, specifically, a number of heartbeats HR, MWSA value, and RSA value are sampled by the execution of steps S4–S7 in the main flow. Next, data on the actually running car, i.e., the continuous driving time S, orientation variance parameter 1/σa, speed variance parameter 1/σu, current running road information D, and travelling distance L are measured by the execution of steps S8–S13. Next, driver's depressed mental conditions during the drive, i.e., sleepiness, tiredness, and impatience of the driver are detected by the execution of steps S14, S15, and S16. In other words, if it is determined, based on the physiological data on the driver and the data on the actually running car, that the driver is sleepy, step S111 is executed to generate a sleepiness alarm. Also, if it is determined, based on the physiological data on the driver and the data on the actually running car, that the driver is tired, the step S126 is executed to generate a tiredness alarm. Further, if it is determined, based on the physiological data on the driver and the data on the actually running car that the driver is impatient, step S135 is executed to generate an impatience alarm.

Figure 15:
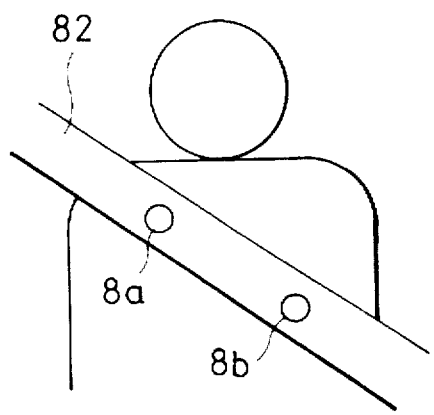
FIGS. 15–17 show other examples depicting how MT pickups of the cardiac rate measuring apparatus according to the present invention are attached.
Figure 16:
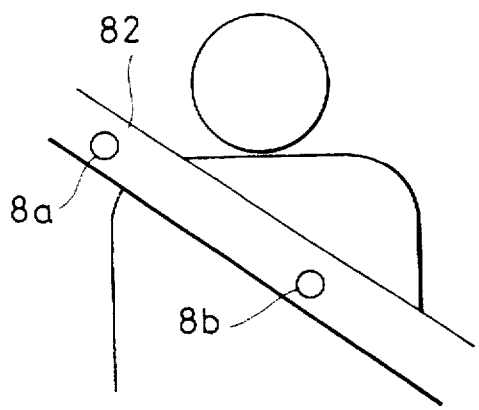
Figure 17:
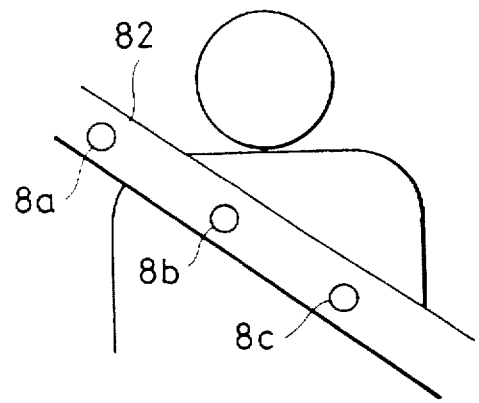

It should be noted that while the embodiment of FIG. 3 shows a single MT pickup 8 mounted on the seat belt 82, a plurality of MT pickups may be mounted at different positions on the seat belt 82 as shown in FIGS. 15–17.

FIG. 15 shows an example in which two MT pickups 8a and 8b are mounted at two positions on the seat belt 82 at which the driver, when seated, is in contact with them.

Figure 18:
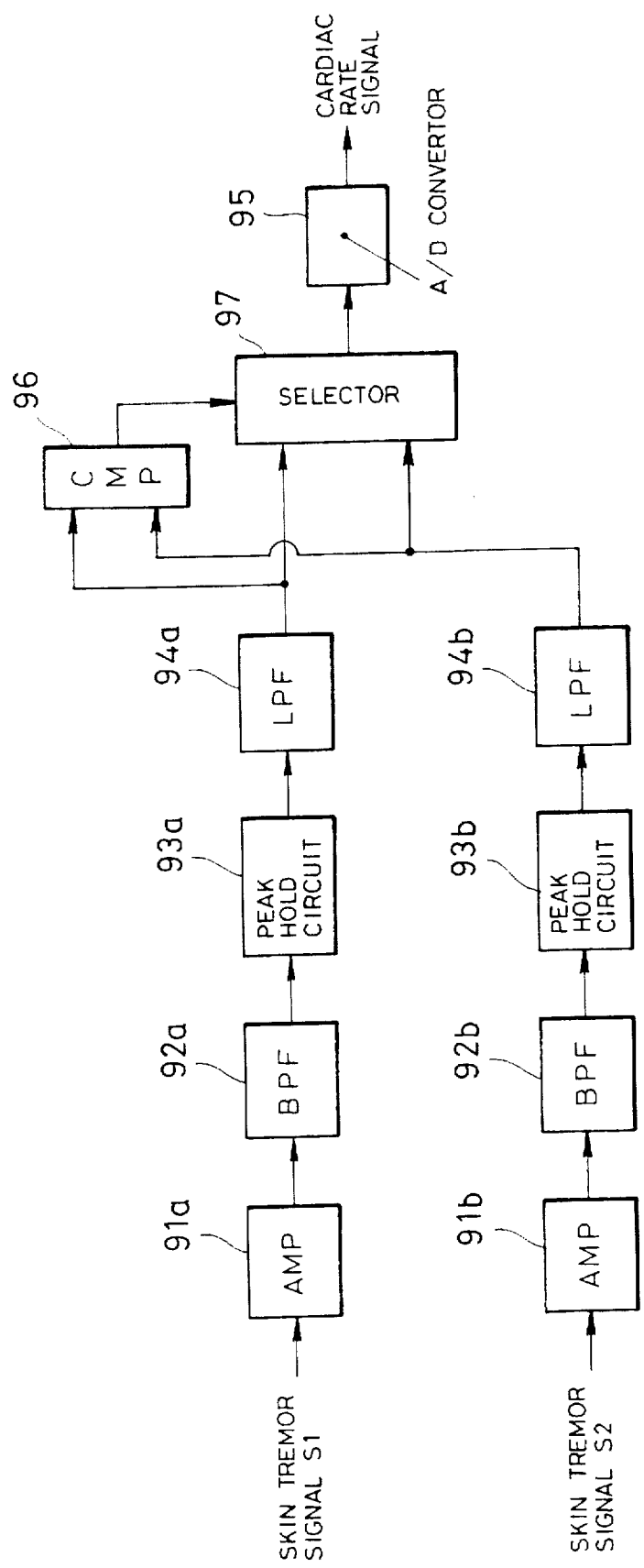

FIG. 18 shows an exemplary configuration of the cardiac rate detector circuit 9 which may be adopted when the MT pickups 8a and 8b as shown in FIG. 15 are employed.

Referring specifically to FIG. 18, skin tremor signals S1 and S2 generated respectively from the MT pickup 8a and 8b are supplied to amplifiers 91a and 91b, respectively. In the block diagram shown in FIG. 18, the amplifier 91a, BPF 92a, peak hold circuit 93a, and LPF 94a, as well as the amplifier 91b, BPF 92b, peak hold circuit 93b, and LPF 94b have the same functions as the corresponding amplifier 91, BPF 92, peak hold circuit 93, and LPF 94 shown in FIG. 4. Therefore, the skin tremor signal S1 generated from the MT pickup 8a is converted to a cardiac rate signal by a series configuration of the amplifier 91a, BPF 92a, peak hold circuit 93a, and LPF 94a, and the cardiac rate signal is supplied to a comparator 96 and a selector 97. On the other hand, the skin tremor signal S2 generated from the MT pickup 8b is also converted to a cardiac rate signal by a series configuration of the amplifier 91b, BPF 92b, peak hold circuit 93b, and LPF 94b, and the cardiac rate signal is supplied to the comparator 96 and the selector 97. A combination of the comparator 96 and the selector 97 selects a cardiac rate signal at higher level from the cardiac rate signals S1, S2 input from the LPF 94a and LPF 94b, and supplies the selected cardiac rate signal to an A/D convertor 95.

In summary, with the configurations shown in FIGS. 15 and 18, one of the skin tremor signals S1, S2 from the two pickups 8a and 8b having a higher detection sensitivity is used for the detection of the cardiac rate signal.

Figure 19:
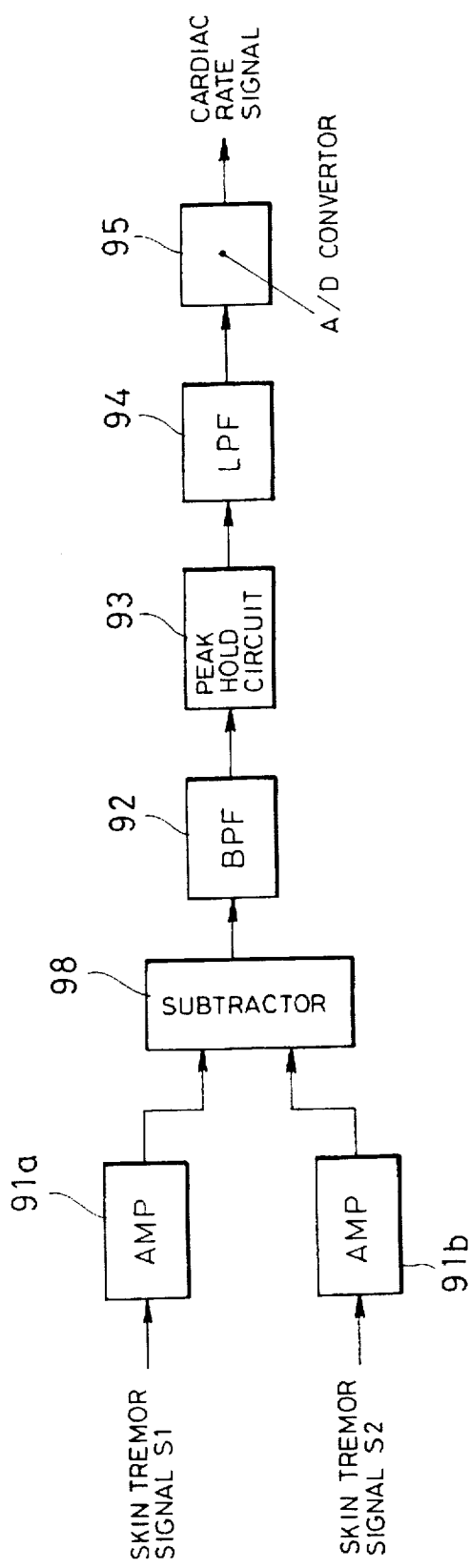

FIG. 16 shows another example of employing two MT pickups, wherein an MT pickup 8a is mounted at a position on a seat belt 82 at which the driver does not contact with the MT pickup 8a, and an MT pickup 8b is mounted at a position on the seat belt 82 at which the driver, when seated, is in contact with the MT pickup 8b. FIG. 19 shows an exemplary configuration of the cardiac rate detector circuit 9 which may be adopted when the MT pickups mounted as shown in FIG. 16 are employed. Referring specifically to FIG. 19, skin tremor signals S1 and S2 respectively generated from the MT pickups 8a and 8b are supplied to a subtractor 98 through amplifiers 91a and 91b, respectively. The subtractor 98 subtracts the level of one signal from the level of the other, and supplies the derived difference skin tremor signal to a BPF 92. In the configuration of FIG. 19, the BPF 92, peak hold circuit 93, LPF 94, and A/D convertor 95 have the same functions as the respective corresponding functional modules shown in FIG. 4.

Specifically, according to the configurations shown in FIGS. 16 and 19, by subtracting the skin tremor signal S1 supplied from the MT pickup 8a mounted at the position at which the driver does not contact with the MT pickup 8a from the skin tremor signal S2 supplied from the MT pickup 8b mounted at the position at which the driver is in contact with the MT pickup 8b, mixed noise components in the same phase can be removed from the skin tremor signal.

FIG. 17 shows a further example in which three MT pickups 8a, 8b, and 8c are employed such that the MT pickup 8a is mounted at a position on a seat belt 82 at which the driver does not contact with it, and the MT pickups 8b and 8c are mounted at positions on the seat belt 82 at which the driver, when seated, is in contact with them.

FIG. 20 shows an exemplary configuration of the cardiac rate detector circuit 9 which may be adopted when the three MT pickups mounted as shown in FIG. 17 are employed.

Referring specifically to FIG. 20, skin tremor signals S1 and S2 respectively generated from the MT pickups 8a and 8b are supplied to a subtractor 98a through amplifiers 91a and 91b, respectively. The subtractor 98a subtracts the level of one signal from the level of the other, and supplies the derived difference skin tremor signal to a BPF 92a. In the configuration of FIG. 20, the BPF 92a, peak hold circuit 93a, and LPF 94a have the same functions as the respective functional modules designated the same reference numerals in FIG. 18.

On the other hand, skin tremor signals S2 and S3 respectively generated from the MT pickups 8b and 8c are supplied to a subtractor 98b through amplifiers 91b and 91c, respectively. The subtractor 98b subtracts the level of one signal from the level of the other, and supplies the derived difference skin tremor signal to a BPF 92b. In the configuration of FIG. 20, the BPF 92b, peak hold circuit 93b, and LPF 94b have the same functions as the respective functional modules designated the same reference numerals in FIG. 18. A combination of a comparator 96 and a selector 97 selects a cardiac rate signal at higher level from the cardiac rate signals S1, S2 input from the LPF 94a and LPF 94b, and supplies the selected cardiac rate signal to an A/D convertor 95. In summary, with the configurations shown in FIGS. 17 and 20, a skin tremor signal having a higher detection sensitivity is used for the detection of the cardiac rate signal, while noise components in the same phase mixed in the skin tremor signal are reduced.

As described above, the cardiac rate measuring apparatus according to the present invention detects skin tremors occurring on the surface of the skin of a body, and holds level peak values of the skin tremors to generate an envelope waveform signal which is used as a cardiac rate signal.

It will be appreciated that, according to the present invention, since the cardiac rate can be measured for a driver with a skin tremor sensor, i.e., the so-called MT pickup, mounted on a seat belt, which is capable of detecting skin tremors occurring on the surface of the skin of the driver's body through clothes of the driver and the seat belt, the cardiac rate measurement can be favorably accomplished without troubling the driver.

What is claimed is:

1. A cardiac rate measuring apparatus comprising:

skin tremor detecting means for detecting skin tremors corresponding to heartbeats of a body to generate a skin tremor signal; and cardiac rate detecting means for holding level peak values of said skin tremor signal to generate an envelope waveform signal and for detecting said envelope waveform signal as a cardiac rate signal, wherein said skin tremor detecting means are mounted at a first position on a seat belt of a car at which the body of a driver contacts with said tremor detecting means and at a second position on the seat belt of the car at which the body of the driver does not contact with said tremor detecting means, and said cardiac rate detecting means subtracts a skin tremor signal generated from said skin tremor detecting means mounted at said second position from a skin tremor signal generated from said skin tremor detecting means mounted at said first position to generate a difference signal, and holds level peak values of said difference signal to generate an envelope waveform signal as said cardiac rate signal.

* * * * *